US012262933B2

(12) United States Patent
Yang et al.

(10) Patent No.: US 12,262,933 B2
(45) Date of Patent: *Apr. 1, 2025

(54) APPARATUS AND METHOD FOR TARGETED BRONCHIAL DENERVATION BY CRYO-ABLATION

(71) Applicant: Medtronic CryoCath LP, Toronto (CA)

(72) Inventors: Zhongping Yang, Woodbury, MN (US); Linnea R. Lentz, Stacy, MN (US); Rick D. McVenes, Isanti, MN (US); Dan Wittenberger, Blainville (CA)

(73) Assignee: Medtronic CryoCath LP, Toronto (CA)

( * ) Notice: Subject to any disclaimer, the term of this patent is extended or adjusted under 35 U.S.C. 154(b) by 348 days.

This patent is subject to a terminal disclaimer.

(21) Appl. No.: 17/749,704

(22) Filed: May 20, 2022

(65) Prior Publication Data
US 2022/0280217 A1    Sep. 8, 2022

Related U.S. Application Data

(63) Continuation of application No. 16/282,504, filed on Feb. 22, 2019, now Pat. No. 11,344,356.
(Continued)

(51) Int. Cl.
*A61B 18/02* (2006.01)
*A61B 18/00* (2006.01)

(52) U.S. Cl.
CPC .... *A61B 18/02* (2013.01); *A61B 2018/00232* (2013.01); *A61B 2018/00541* (2013.01);
(Continued)

(58) Field of Classification Search
CPC ............ A61B 18/02; A61B 2018/0022; A61B 2018/00232; A61B 2018/0025;
(Continued)

(56) References Cited

U.S. PATENT DOCUMENTS 7,412,977 B2    8/2008  Fields et al.
7,938,123 B2    5/2011  Danek et al.
(Continued)

FOREIGN PATENT DOCUMENTS

EP    3120792 A1    1/2017
EP    3244820 B1    6/2020
(Continued)

OTHER PUBLICATIONS

Yan-Lin Yang, et al., Optimal Esophageal Balloon Volume for Accurate Estimation of Pleural Pressure at End-Expiration and End-Inspiration: an in Vitro Bench Experiment, Intensive Care Medicine Experimental, Aug. 2, 2017 (Aug. 2, 2017), DOI: 10.1186/s40635-017-0148-z, 12 pages.
(Continued)

*Primary Examiner* — Daniel W Fowler
(74) *Attorney, Agent, or Firm* — Michael Best & Friedrich LLP

(57) ABSTRACT

A method for performing bronchial denervation, the method comprising an electromyography system having a cryoablation device with at least two recording electrodes. The electromyography system being configured to calculate a difference between a first electromyogram signal received from the first recording electrode and a second electromyogram signal received from the second recording electrode to generate a recorded electromyogram and compare the recorded electromyogram to a reference electromyogram.

20 Claims, 10 Drawing Sheets

Related U.S. Application Data

(60) Provisional application No. 62/636,416, filed on Feb. 28, 2018.

(52) U.S. Cl.
CPC ............... *A61B 2018/00577* (2013.01); *A61B 2018/00642* (2013.01); *A61B 2018/00839* (2013.01); *A61B 2018/0262* (2013.01)

(58) Field of Classification Search
CPC ........... A61B 2018/00255; A61B 2018/00791; A61B 2018/00863; A61B 2018/00994; A61B 2018/0212; A61B 2018/0262
See application file for complete search history.

(56) References Cited

U.S. PATENT DOCUMENTS

| | | |
|---|---|---|
| 8,088,127 B2 | 1/2012 | Mayse et al. |
| 9,095,321 B2 | 8/2015 | Phelan et al. |
| 9,144,449 B2 | 9/2015 | Burr et al. |
| 10,328,281 B2 | 6/2019 | Stopek |
| 2005/0159788 A1* | 7/2005 | Kress .................... A61B 5/283 607/32 |
| 2007/0255162 A1 | 11/2007 | Abboud et al. |
| 2008/0312644 A1 | 12/2008 | Fourkas et al. |
| 2009/0192505 A1 | 7/2009 | Askew et al. |
| 2009/0205665 A1 | 8/2009 | Tanaka et al. |
| 2009/0299355 A1 | 12/2009 | Bencini et al. |
| 2009/0306644 A1* | 12/2009 | Mayse .................... A61B 18/24 128/898 |
| 2010/0249765 A1 | 9/2010 | Johnston |
| 2011/0118725 A1 | 5/2011 | Mayse et al. |
| 2011/0152855 A1 | 6/2011 | Mayse et al. |
| 2012/0136418 A1 | 5/2012 | Buckley et al. |
| 2012/0310226 A1 | 12/2012 | Fourkas et al. |
| 2013/0190747 A1* | 7/2013 | Koblish ............. A61B 18/1492 606/41 |
| 2015/0141813 A1 | 5/2015 | Weadock |
| 2015/0173673 A1 | 6/2015 | Toth et al. |
| 2015/0265334 A1 | 9/2015 | Franke et al. |
| 2015/0272666 A1 | 10/2015 | Wang |
| 2015/0289931 A1* | 10/2015 | Puryear ............. A61B 18/1492 606/41 |
| 2017/0319853 A1 | 11/2017 | Yamasaki et al. |
| 2019/0026056 A1 | 1/2019 | Wang et al. |
| 2019/0262056 A1 | 8/2019 | Yang et al. |
| 2019/0365452 A1 | 12/2019 | Avitall et al. |
| 2020/0000514 A1 | 1/2020 | Weadock |
| 2020/0060758 A1 | 2/2020 | Rajagopalan et al. |
| 2020/0129220 A1 | 4/2020 | Jung |

FOREIGN PATENT DOCUMENTS

| | | |
|---|---|---|
| WO | 2012019156 A1 | 2/2012 |
| WO | 2012027641 A2 | 3/2012 |
| WO | 2015120325 A1 | 8/2015 |
| WO | 2016033017 A1 | 3/2016 |
| WO | 2016109437 A1 | 7/2016 |
| WO | 2017214183 A1 | 12/2017 |

OTHER PUBLICATIONS

International Search Report and Written Opinion dated Nov. 4, 2021, for corresponding International Application No. PCT/US2021/043178; International Filing Date: Jul. 26, 2021, consisting of 181-pages.

China National Intellectual Property Administration Notice of First Office Action for Application No. 201980016103.8 dated Dec. 29, 2023 (21 pages including English translation).

International Search Report dated May 24, 2019, for International Application No. PCT/CA2019/050226 filed on Feb. 26, 2019; Consisting of 8 pages.

European Patent Office, Supplementary European Search Report, dated Nov. 2, 2021, for corresponding European Application No. EP 19761431; consisting of 7 pages.

China National Intellectual Property Administration Second Office Action for Application No. 201980016103.8 dated Aug. 1, 2024 (22 pages including English translation).

China National Intellectual Property Administration Third Office Action for Application No. 201980016103.8 dated Dec. 18, 2024 (8 pages including English translation).

* cited by examiner

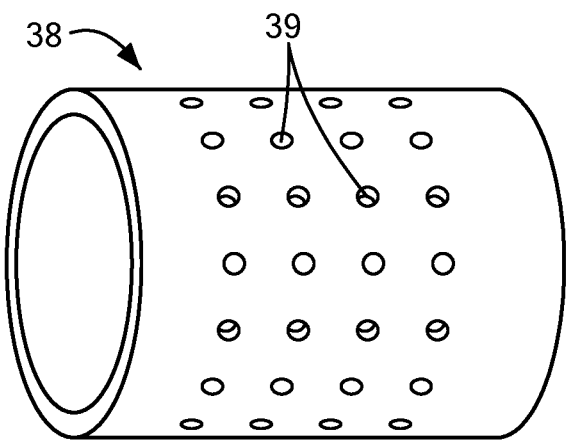 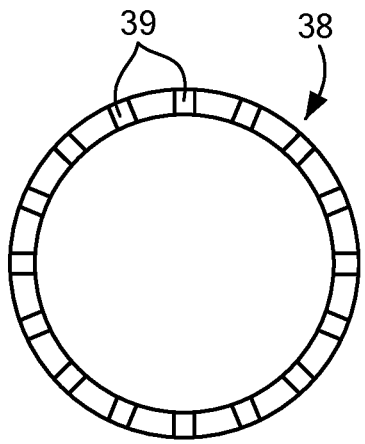
*FIG. 5A*  *FIG. 5B*
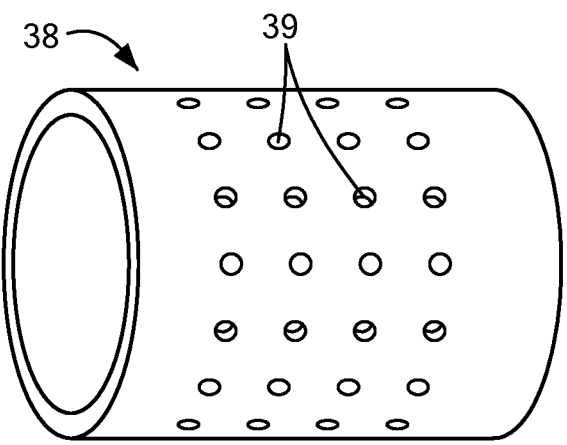 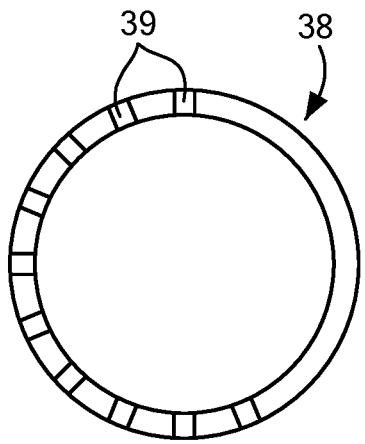
*FIG. 6A*  *FIG. 6B*
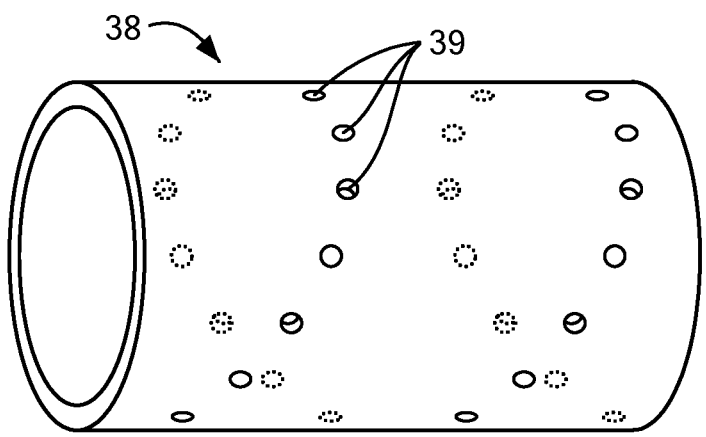 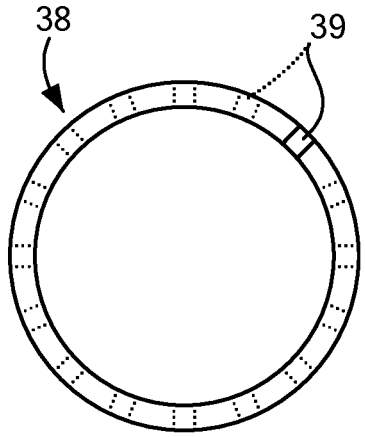
*FIG. 7A*  *FIG. 7B*

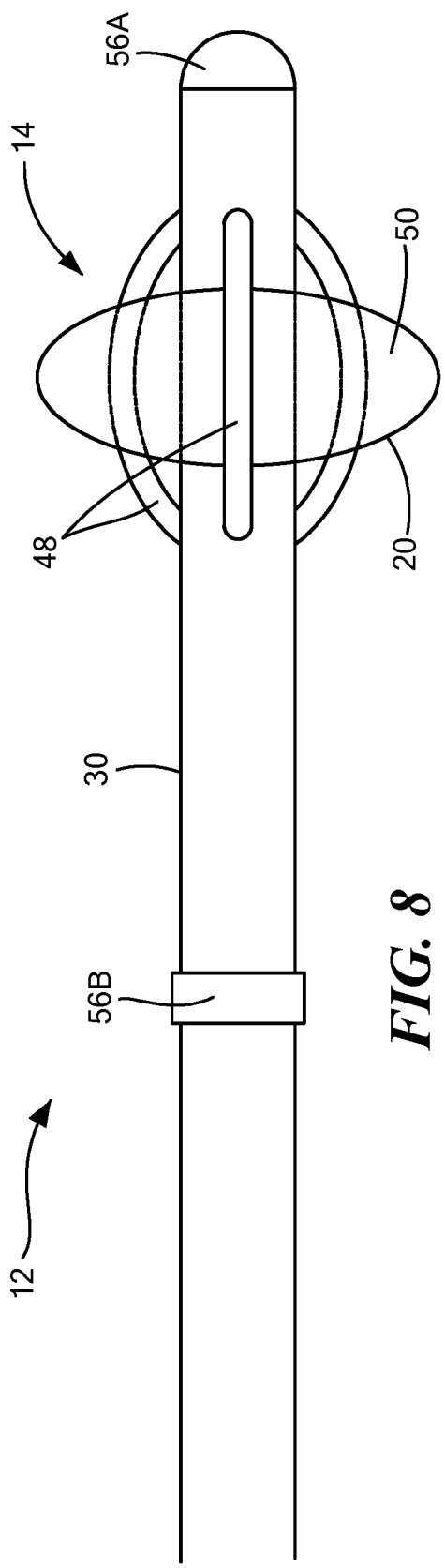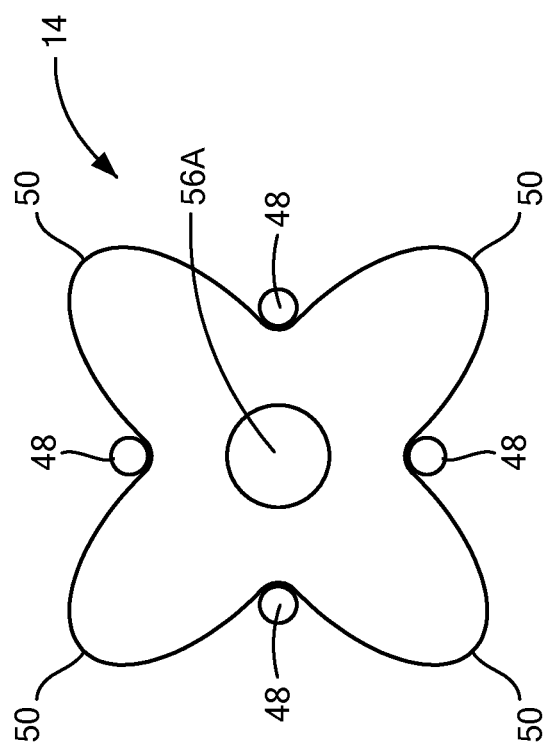
FIG. 8
FIG. 9

APPARATUS AND METHOD FOR TARGETED BRONCHIAL DENERVATION BY CRYO-ABLATION

CROSS-REFERENCE TO RELATED APPLICATION

This application is a Continuation of U.S. application Ser. No. 16/282,504, filed Feb. 22, 2019 and this application claims the benefit of U.S. Application Ser. No. 62/636,416, filed Feb. 28, 2018.

FIELD

The present technology is generally related to devices, systems, and methods for treating pulmonary conditions, such as chronic obstructive pulmonary disease (COPD) and asthma, by denervating bronchial tissue using cryoablation.

BACKGROUND

Chronic obstructive pulmonary disease (COPD) is a chronic inflammatory lung disease that results in obstructed airflow within the lungs, and the term is also used to refer to a family of pulmonary conditions, such as emphysema and chronic bronchitis. COPD is the fourth leading cause of death, with approximately one-third of all health-related expenses being associated with the condition. Asthma is believed to be a risk factor for developing COPD, and patients with COPD may be more likely to develop heart disease, lunch cancer, and other conditions. Research indicates that COPD causes epithelial metaplasia, mucous metaplasia, fibrosis, increase in smooth muscle mass, and other conditions that, in addition to the contractile nature of bronchial smooth muscle, contribute to airway obstruction. Additionally, bronchial smooth muscle in patients with COPD is infiltrated by inflammatory cytokines, proteases, and growth factors, which further exacerbates airway obstruction.

Denervation, or neural modulation, of the parasympathetic nervous system (PSNS) is a relatively new technique for treating conditions such as hypertension and cardiovascular disease in a minimally invasive way. However, there has been little research indicating the efficacy of denervation for other conditions, such as those affecting the lungs. Further, when performing denervation, care must be taken to avoid damaging non-target tissue.

SUMMARY

Some embodiments advantageously provide devices, systems, and methods for treating pulmonary conditions, such as COPD, by denervating bronchial tissue using cryoablation. In one embodiment, a device for bronchial denervation comprises: an elongate body having a distal portion and a proximal portion opposite the distal portion; a treatment element at the distal portion of the elongate body; and a first recording electrode located distal to the treatment element and a second recording electrode located proximal to the treatment element, the first and second recording electrodes being configured to record electromyograms.

In one aspect of the embodiment, the treatment element includes at least one balloon. In one aspect of the embodiment, the treatment element includes an equatorial portion, the treatment element further including a fluid delivery element within the at least one balloon, the fluid delivery element having a plurality of orifices that are aligned with the equatorial portion of the treatment element. In one aspect of the embodiment, the plurality of orifices includes at least twenty-four orifices radially arranged about the fluid delivery element, each of the at least twenty-four orifices having a diameter of between approximately 0.0005 inch and approximately 0.0015 inch.

In one aspect of the embodiment, the at least twenty-four orifices are radially arranged about an entirety of a circumference of the fluid delivery element.

In one aspect of the embodiment, the at least twenty-four orifices are radially arranged about a portion of a circumference of the fluid delivery element.

In one aspect of the embodiment, the at least twenty-four orifices are helically arranged about an entirety of a circumference of the fluid delivery element.

In one aspect of the embodiment, the treatment element includes: a balloon having a plurality of lobes; and a plurality of splines extending parallel to the longitudinal axis of the elongate body, the plurality of splines alternating with the plurality of lobes.

In one embodiment, a system for bronchial denervation comprises: a cryoablation device including a treatment element and at least one recording electrode; an electromyography system in communication with the at least one recording electrode; and a control unit in fluid communication with the cryoablation device.

In one aspect of the embodiment, the cryoablation device further includes a longitudinal axis, the treatment element including: a balloon having a plurality of lobes; and a plurality of splines extending parallel to the longitudinal axis of the cryoablation device and between the plurality of lobes.

In one aspect of the embodiment, the treatment element includes a flexible portion that is transitionable between an at least substantially linear first configuration and an expanded second configuration, the flexible portion having a helical configuration when in the expanded second configuration.

In one aspect of the embodiment, the at least one recording electrode includes a first recording electrode located distal to the treatment element and a second recording electrode located proximal to the treatment element.

In one aspect of the embodiment, the electromyography system includes processing circuitry configured to: receive electromyogram signals from the at least one recording electrode; calculate a difference between a first electromyogram signal received from the first recording electrode and a second electromyogram signal received from the second recording electrode to generate a recorded electromyogram; and compare the recorded electromyogram to a reference electromyogram.

In one aspect of the embodiment, the processing circuitry is further configured to determine whether denervation has occurred in an area of targeted tissue proximate the treatment element based on the comparison between the recorded electromyogram and the reference electromyogram.

In one aspect of the embodiment, the processing circuitry is further configured to generate an alert when the processing circuitry has determined that denervation has occurred in the area of targeted tissue proximate the treatment element.

In one aspect of the embodiment, the control unit includes a coolant source, the coolant source being in fluid communication with the treatment element.

In one embodiment, a method for performing bronchial denervation comprises: positioning a treatment element of a cryoablation device within a bronchus of a patient's lung; expanding the treatment element such that at least a portion of the treatment element is in contact with at least a portion of at least one of bronchial tissue and nerves innervating the bronchial tissue; circulating coolant within the treatment element to reduce a temperature of the treatment element to a temperature sufficient to cryoablate the at least a portion of the at least one of bronchial tissue and nerves innervating bronchial tissue; recording at least one electromyogram signal from the at least a portion of the at least one of bronchial tissue and nerves innervating bronchial tissue with each of a first recording electrode and a second recording electrode; and transmitting the recorded at least one electromyogram signal to an electromyography system.

In one aspect of the embodiment, the method further comprises: calculating a difference between the at least one electromyogram signal received from the first recording electrode and the at least one electromyogram signal received from the second recording electrode to generate a recorded electromyogram; comparing the recorded electromyogram to a reference electromyogram; determining whether denervation has occurred in the at least a portion of the at least one of bronchial tissue and nerves innervating bronchial tissue based on the comparison; and discontinuing the circulation of coolant within the treatment element when it is determined that denervation has occurred in the at least a portion of the at least one of bronchial tissue and nerves innervating bronchial tissue.

In one aspect of the embodiment, the method further comprises: generating an alert when it is determined that denervation has occurred in the at least a portion of the at least one of bronchial tissue and nerves innervating bronchial tissue.

In one aspect of the embodiment, the treatment element includes at least one balloon, expanding the treatment element including inflating the balloon.

In one aspect of the embodiment, the at least one balloon includes: a balloon having a plurality of lobes; and a plurality of splines extending between the plurality of lobes.

In one embodiment, a method for performing bronchial denervation, the method comprising an electromyography system having a cryoablation device with at least two recording electrodes. The electromyography system being configured to calculate a difference between a first electromyogram signal received from the first recording electrode and a second electromyogram signal received from the second recording electrode to generate a recorded electromyogram and compare the recorded electromyogram to a reference electromyogram.

In one aspect of the embodiment, the method further comprises transmitting the first electromyogram signal and the second electromyogram signal to the electromyography system.

In one aspect of the embodiment, the at least two recording electrodes includes a first recording electrode and a second recording electrode, when the cryoablation device is performing a cryoablation procedure the first recording electrode and the second recording electrode are continuously transmitting signals to the electromyography system.

In one aspect of the embodiment, the method further includes calculating a voltage difference between the first electromyogram signal and the second electromyogram signal.

In one aspect of the embodiment, the at least two recording electrodes includes a first recording electrode and a second recording electrode and before the cryoablation device is performing a cryoablation procedure, the first recording electrode and the second recording electrode are continuously transmitting signals to the electromyography system.

In one aspect of the embodiment, the at least two recording electrodes includes a first recording electrode and a second recording electrode and while the cryoablation device performs a cryoablation procedure and after the cryoablation device performs a cryoablation procedure, the first recording electrode and the second recording electrode are continuously transmitting signals to the electromyography system.

In one aspect of the embodiment, the at least two recording electrodes includes a first recording electrode and a second recording electrode. The calculation further includes calculating a difference between the first electromyogram signal received from the first recording electrode and the second electromyogram signal received from the second recording electrode before a cryoablation procedure to generate a first recorded electromyogram and calculating the difference between the first electromyogram signal received from the first recording electrode and the second electromyogram signal received from the second recording electrode after cryoablation to generate a second recorded electromyogram.

In one aspect of the embodiment, the method further comprises calculating the difference between the first recorded electromyogram and the second recorded electromyogram.

In one aspect of the embodiment, the method further comprises comparing the calculated difference between the first recorded electromyogram and the second recorded electromyogram with a reference electromyogram.

In one aspect of the embodiment, the method further comprises determining whether denervation has occurred based on the comparison between the difference between the first recorded electromyogram and the second recorded electromyogram with the reference electromyogram.

In one aspect of the embodiment, the electromyography system determines that denervation has occurred when the comparison between the difference between the first recorded electromyogram and the second recorded electromyogram with the reference electromyogram exceeds a threshold difference.

In one aspect of the embodiment, the method further comprises generating an alert when the electromyography system determines that denervation has occurred.

In one aspect of the embodiment, the alert is an audible or visual alert.

In one embodiment, a method for performing bronchial denervation where the method comprises a cryoablation device including a treatment element and a first recording electrode and a second recording electrode and an electromyography system in communication with the at least the first recording electrode and the second recording electrode. The electromyography system including processing circuitry configured to receive electromyogram signals from the first recording electrode and the second recording electrode, calculate a difference between a first electromyogram signal received from the first recording electrode and a second electromyogram signal received from the second recording electrode to generate a recorded electromyogram, and compare the recorded electromyogram to a reference electromyogram.

In one aspect of the embodiment, the processing circuitry is further configured to determine whether denervation has occurred in an area of tissue based on the comparison between the recorded electromyogram and the reference electromyogram.

In one aspect of the embodiment, the processing circuitry is further configured to generate an alert when the processing circuitry has determined that denervation has occurred in an area of tissue.

In one embodiment, a method for performing bronchial denervation, the method comprising positioning a treatment element proximate an area of targeted tissue, expanding the treatment element such that at least a portion of the treatment element is in contact the area of targeted tissue, circulating a coolant within the treatment element to reduce a temperature of the treatment element to a temperature sufficient to cryoablate at least a portion of the area of targeted tissue, recording at least one electromyogram signal from the at least a portion of the area of targeted tissue with each of a first recording electrode and a second recording electrode, transmitting the recorded at least one electromyogram signal to an electromyography system, calculating a difference between the at least one electromyogram signal received from the first recording electrode and the at least one electromyogram signal received from the second recording electrode to generate a recorded electromyogram, and comparing the recorded electromyogram to a reference electromyogram.

In one aspect of the embodiment, the method further comprises determining whether denervation has occurred in the at least a portion of the area of targeted tissue based on the comparison and discontinuing the circulation of the coolant within the treatment element when it is determined that denervation has occurred in the area of targeted tissue.

In one aspect of the embodiment, the method further comprises generating an alert when it is determined that denervation has occurred in the at least a portion of the area of targeted tissue.

In one aspect of the embodiment, the electromyography system further includes processing circuitry configured to determine whether denervation has occurred in the area of targeted tissue based on the comparison between the recorded electromyogram and the reference electromyogram.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 5A shows a side view of an exemplary embodiment of a fluid delivery element in accordance with the present disclosure;

FIG. 5B shows a cross-sectional view of the fluid delivery element of FIG. 5A in accordance with the present disclosure;

FIG. 6A shows a side view of another exemplary embodiment of a fluid delivery element in accordance with the present disclosure;

FIG. 6B shows a cross-sectional view of the fluid delivery element of FIG. 6A in accordance with the present disclosure;

FIG. 7A shows a side view of another exemplary embodiment of a fluid delivery element in accordance with the present disclosure;

FIG. 7B shows a cross-sectional view of the fluid delivery element of FIG. 7A in accordance with the present disclosure;

FIG. 8 shows a side view of another exemplary cryoablation device in accordance with the present disclosure;

FIG. 9 shows a front view of the exemplary embodiment of the cryoablation device of FIG. 8 in accordance with the present disclosure;

DETAILED DESCRIPTION

Figure 1:
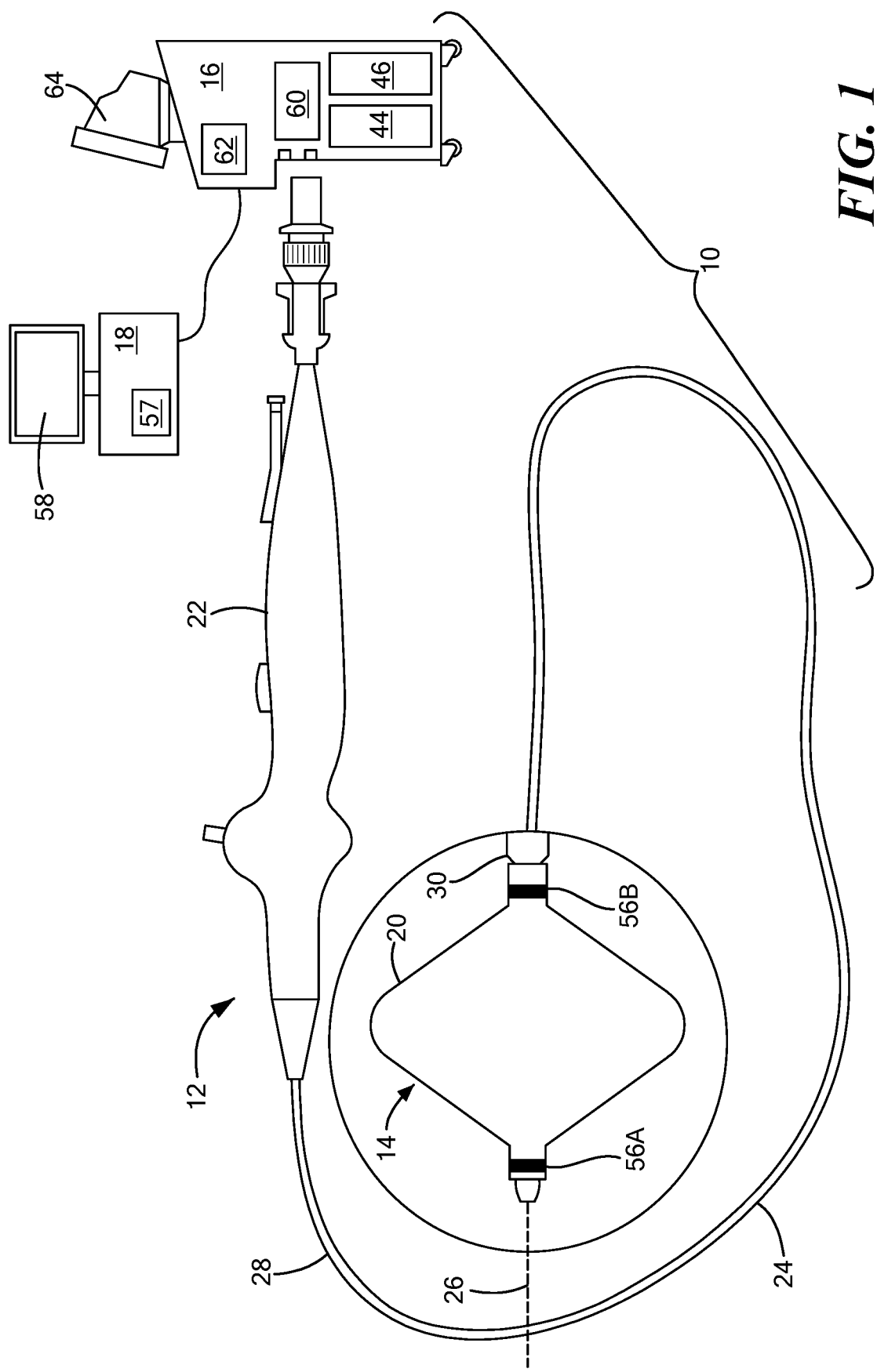
FIG. 1 shows an exemplary system for bronchial denervation; the system including a cryoablation device.

Before describing in detail exemplary embodiments, it is noted that the embodiments reside primarily in combinations of apparatus components and processing steps related to performing a denervation procedure. Accordingly, the system and method components have been represented where appropriate by conventional symbols in the drawings, showing only those specific details that are pertinent to understanding the embodiments of the present disclosure so as not to obscure the disclosure with details that will be readily apparent to those of ordinary skill in the art having the benefit of the description herein. Moreover, while certain embodiments or figures described herein may illustrate features not expressly indicated in other figures or embodiments, it is understood that the features and components of the system and devices disclosed herein are not necessarily exclusive of each other and may be included in a variety of different combinations or configurations without departing from the scope and spirit of the invention.

As used herein, relational terms, such as "first" and "second," "top" and "bottom," and the like, may be used solely to distinguish one entity or element from another entity or element without necessarily requiring or implying any physical or logical relationship or order between such entities or elements. The terminology used herein is for the purpose of describing particular embodiments only and is not intended to be limiting of the concepts described herein. As used herein, the singular forms "a", "an" and "the" are intended to include the plural forms as well, unless the context clearly indicates otherwise. It will be further understood that the terms "comprises," "comprising," "includes" and/or "including" when used herein, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having a meaning that is consistent with their meaning in the context of this specification and the relevant art and will not be interpreted in an idealized or overly formal sense unless expressly so defined herein.

In embodiments described herein, the joining term, "in communication with" and the like, may be used to indicate electrical or data communication, which may be accomplished by physical contact, induction, electromagnetic radiation, radio signaling, infrared signaling or optical signaling, for example. One having ordinary skill in the art will appreciate that multiple components may interoperate and modifications and variations are possible of achieving the electrical and data communication.

The parasympathetic nervous system (PSNS), one branch of the autonomic nervous system, is involved in the parasympathetic control of the lungs. Activation of the PSNS causes postganglionic parasympathetic fibers to release acetylcholine, which results in constriction of the smooth muscle surrounding the bronchi and, in turn, the reduction of airflow. Denervation of the bronchi of the lung using cryoablation may be a safe and effective means for treating COPD and asthma. Many other larger nerves (for example, between 100 and 250 μm) are located within 5 mm of the inner surface of the bronchi. As discussed herein, cryoablating target nerve tissue in or along the bronchial wall radially outward from a tissue location may reduce airway resistance through the bronchus. Using cryoablation may minimize structural tissue damage in the bronchial wall of the airway while denervating parasympathetic nerve(s) around the bronchi and decreasing activity (and constriction) of the smooth muscle.

Referring now to FIG. 1, an exemplary medical system 10 for bronchial denervation is shown. New research indicates that denervation within the lung using cryoablation is a safe and effective means for treating conditions such as COPD and asthma and, consequentially, for potentially reducing the risk of developing other conditions, such as heart disease and lung cancer. In one embodiment, the medical system 10 generally includes a treatment device, such as a cryoablation device 12, having one or more treatment elements 14, and a control unit 16 in communication with the cryoablation device 12. In one embodiment, the medical system 10 also includes an electromyography system 18 in communication with the cryoablation device 12 and the control unit 16. Although the cryoablation device 12 is described herein as operating to reduce the temperature of target tissue in order to ablate nerves within the lungs, it will be understood that the cryoablation device 12 also may be used with one or more additional modalities, such as radiofrequency (RF) ablation, pulsed field ablation, ultrasound ablation, microwave ablation, or the like. Additionally, the cryoablation device 12 may be used for treatment, denervation, or nerve modulation of other locations within the patient's body, such as the heart.

The one or more treatment elements 14 are configured to deliver cryogenic therapy, and may further be configured to deliver radiofrequency energy, pulsed field ablation energy, or the like for energetic transfer with the area of targeted tissue, such as pulmonary tissue. In particular, the treatment element(s) 14 are configured to reduce the temperature of adjacent tissue in order to perform cryotreatment and/or cryoablation and, consequently, denervation. For example, the treatment elements(s) 14 may include one or more balloons 20 (as shown in FIG. 1) within which a coolant may be circulated in order to reduce the temperature of the balloon 20. Additionally, the treatment element(s) 14 may include other thermally and/or electrically-conductive components, such as one or more electrodes in communication with the control unit 16 (not shown).

Figure 2:
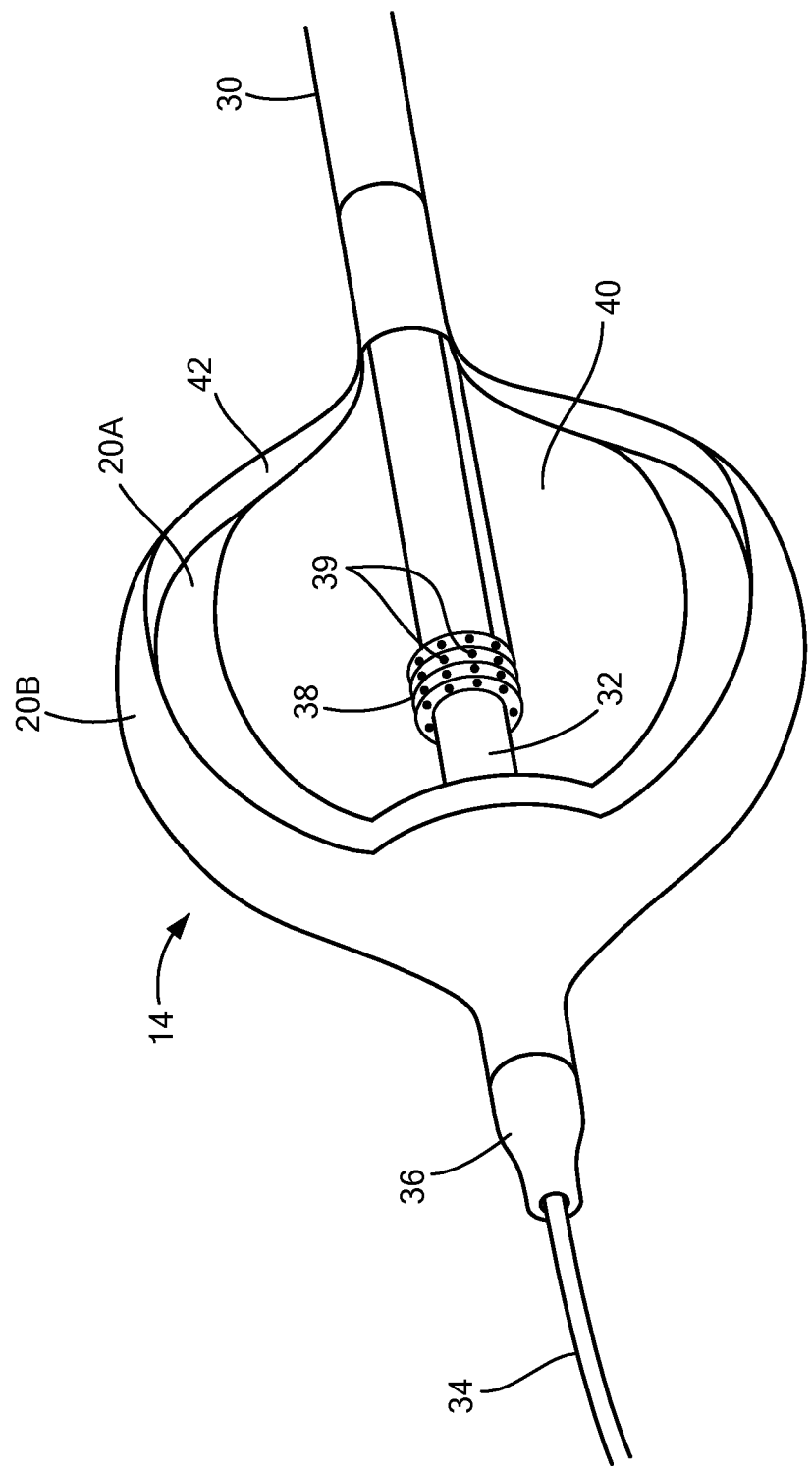
FIG. 2 shows a partial cross-sectional view of an exemplary cryoablation device in accordance with the present disclosure.

In the embodiment shown in FIGS. 1 and 2, the cryoablation device 12 includes a handle 22 and an elongate body 24 coupled to the handle 22. The elongate body 24 is sized and configured to be passable through a patient's vasculature and/or positionable proximate to a tissue region for diagnosis or treatment, such as a catheter, sheath, or intravascular introducer. The elongate body 24 defines a longitudinal axis 26, a proximal portion 28, and a distal portion 30, and may further include one or more lumens disposed within the elongate body 24 that provide mechanical, electrical, and/or fluid communication between the proximal portion 28 of the elongate body 24 and the distal portion 30 of the elongate body 24. Further, the treatment element(s) 14 (such as the balloon(s) 20 shown in FIGS. 1 and 2) are coupled to the elongate body distal portion 30. In one embodiment, the cryoablation device 12 further includes a shaft 32 that is longitudinal movable within a lumen of the elongate body 24, such that the shaft 32 may be advanced or retracted within the elongate body 24, and this movement of the shaft 32 may affect the shape and configuration of the treatment element(s) 14. For example, the cryoablation device 12 may include one treatment element 14, and the shaft 32 may be fully advanced when the treatment element 14 is deflated and in a delivery (or first) configuration wherein the treatment element 14 has a minimum diameter suitable, for example, for retraction of the cryoablation device 12 within a sheath for delivery to and removal from the targeted tissue site. Conversely, when the treatment element 14 is inflated or expanded and in a treatment (or second) configuration, the shaft 32 may be advanced or retracted over a distance that affects the size and configuration of the inflated or expanded treatment element 14. Further, the shaft 32 may include a guidewire lumen through which a sensing device, mapping device, guidewire 34, or other system component may be located and extended from the distal end of the cryoablation device 12 (for example, from the distal portion 36 of the shaft 32). When expanded, the treatment element(s) 14 are sized and configured to fit within a targeted bronchus. For example, the expanded treatment element(s) 14 may have a maximum outer diameter of between approximately 5 mm and approximately 40 mm (±2 mm).

In one embodiment, the treatment element 14 includes two balloons: an inner (or first) balloon 20A and an outer (or second) balloon 20B. However, it will be understood that the treatment element 14 may include any number of balloons. In the embodiment shown in FIG. 2, a proximal portion of the treatment element 14 is coupled to the distal portion 30 of the elongate body 24 and a distal portion of the treatment element 14 is coupled to a distal portion 36 of the shaft 32. The cryoablation device 12 also includes one or more nozzles, orifices, or other fluid delivery elements 38 for delivering fluid (for example, coolant) to an interior chamber 40 of the treatment element 14. For example, fluid may be delivered to the interior chamber 40 of the inner balloon 20A and/or to the interior chamber of the outer cryoballoon 20B (that is, to the interstitial space 42 between the inner 20A and outer 20B balloons). For simplicity, coolant will be referred to herein as being delivered to the interior chamber 40 of the treatment element 14. During operation, coolant may flow from a coolant supply reservoir 44 through a coolant delivery conduit within the elongate body 24 of the cryoablation device 12 to the distal portion 30, where the coolant may then enter the interior chamber 40 of the treatment element 14, such as through the one or more fluid delivery elements 38, where the coolant may expand to cool the balloon(s) 20. Expanded coolant may then pass from the interior chamber 40 of the treatment element 14 to a coolant recovery reservoir 46 and/or scavenging system through a coolant recovery conduit.

Figure 3:
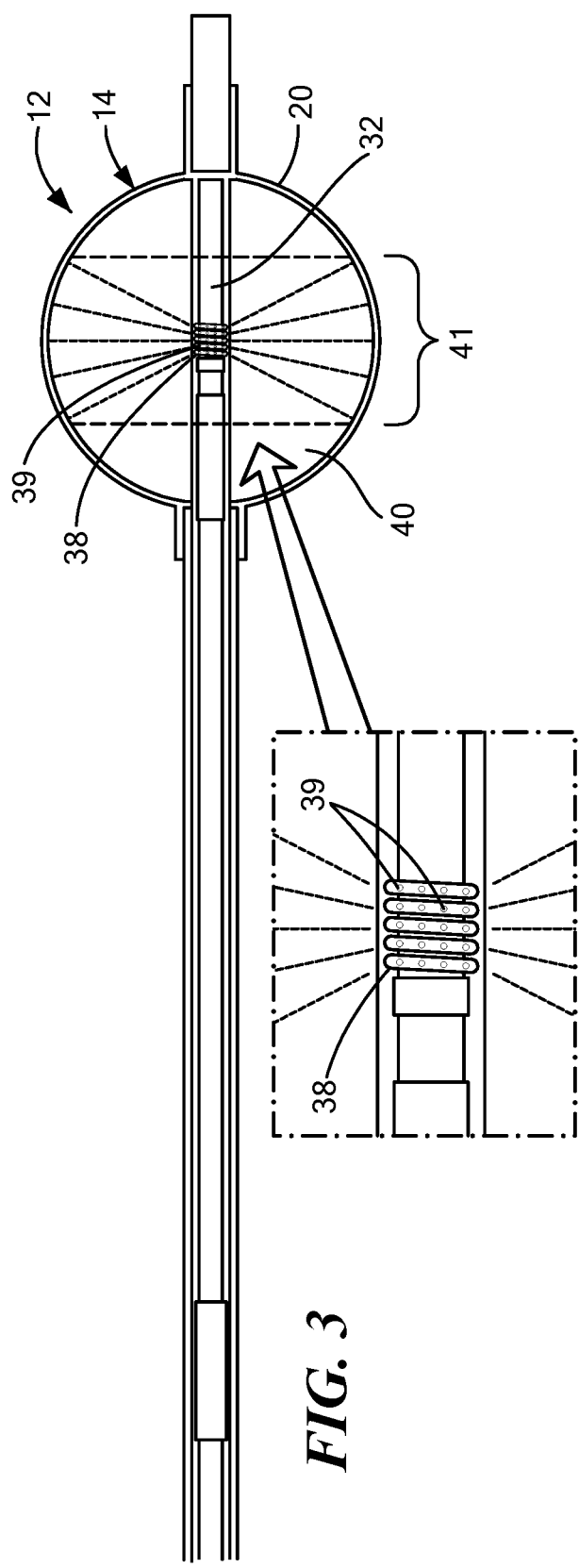
FIG. 3 shows an exemplary cryoablation device having an exemplary embodiment of a fluid delivery element in accordance with the present disclosure.
Figure 4:
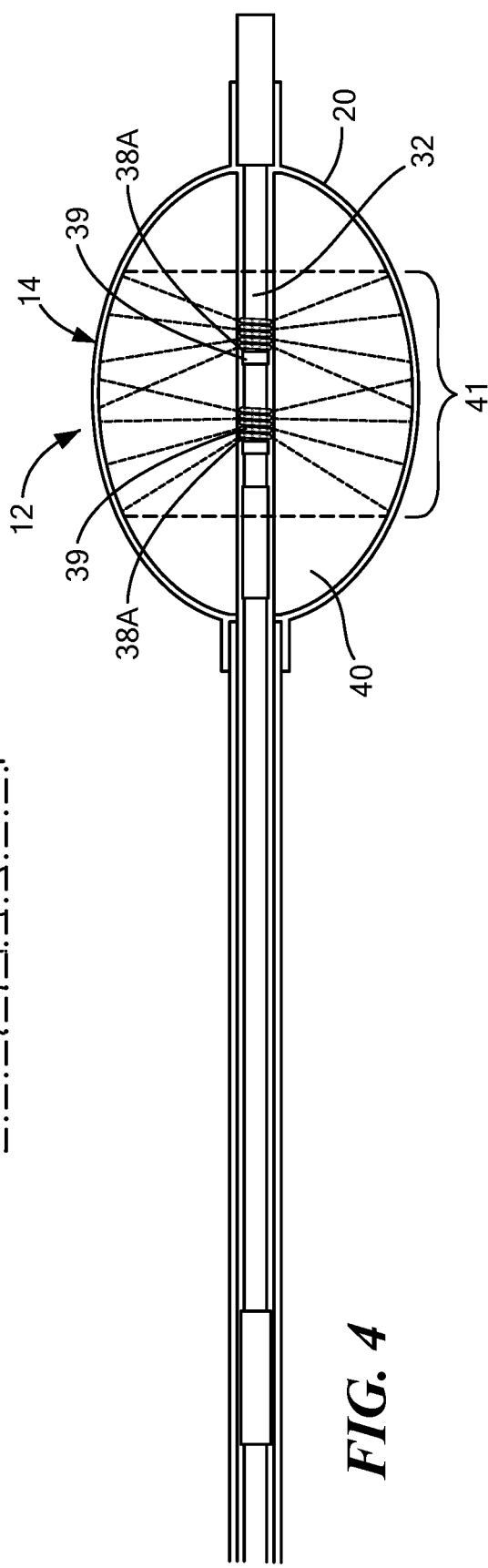
FIG. 4 shows an exemplary cryoablation device having another exemplary embodiment of a fluid delivery element in accordance with the present disclosure.

Referring now to FIGS. 3 and 4, exemplary embodiments of a cryoablation device 12 with at least one fluid delivery element 38 are shown. In one embodiment, the medical device 12 is generally as shown and described in FIGS. 1 and 2, and each fluid delivery element 38 includes a fluid delivery conduit that is wound or coiled about the shaft 32 at least once. In one non-limiting example, as shown in FIG. 3, the cryoablation device 12 includes one fluid delivery element 38 that includes a plurality of orifices 39 in the coiled portion that are radially arranged about the fluid delivery element 38, and in some embodiments the shaft 32. In one non-limiting example, the fluid delivery element 38 includes twenty-four orifices 39, or more, each orifice 39 having a diameter of between approximately 0.0005 inch and approximately 0.0015 inch, and the fluid delivery conduit has a diameter of between approximately 0.005 inch and approximately 0.025 inch. Further, the orifices 39 are located within a center swath or equatorial portion 41 of the treatment element 14 when the treatment element 14 is expanded. In one embodiment, the equatorial portion 41 corresponds to the portion of the balloon(s) 20 at which the balloon(s) 20 have the largest outer diameter when the balloon(s) 20 are inflated, such as when the balloon(s) 20 are fully inflated. Put one way, the equatorial portion 41 extends around the balloon(s) 20 of the treatment element 14 and the fluid delivery element(s) 38 are located within the treatment element 14 at a location that is aligned with the equatorial portion 41. Put another way, the equatorial portion 41 lies in a cross-sectional plane of the treatment element 14 that includes the portion of the treatment element having the largest outer diameter, and the fluid delivery element(s) 38 are located within the equatorial portion 41. Further, if the device includes two balloons 20, in one embodiment the equatorial portion 41 of the first balloon 20A and the equatorial portion 41 of the second balloon 20B are in overlapping or overlaid positions such that the treatment element 14 as a whole defines the equatorial portion 41. In another non-limiting example, as shown in FIG. 4, the cryoablation device 12 includes a first fluid delivery element 38A and a second fluid delivery element 38B, each of which including a plurality of orifices 39 in the coiled portion that are radially arranged about the fluid delivery element, and in some embodiments the shaft 32. In one non-limiting example, each fluid delivery element 38A, 38B includes twenty-four orifices 39, or more, each orifice 39 having a diameter of between approximately 0.0005 inch and approximately 0.0015 inch and the fluid delivery conduit has a diameter of between approximately 0.005 inch and approximately 0.025 inch. The embodiments shown in FIGS. 2-4 are in contrast to presently known devices, such as those used for atrial fibrillation treatment procedures, which typically include a fluid delivery element having eight orifices, each having a diameter of 0.0025 inch. It will be understood that more than twenty-four orifices 39 may be used. Thus, in some embodiments, the device of the present disclosure includes at least one fluid delivery element 38 with more orifices 39 than presently known devices, and with each orifice 39 having a smaller diameter than presently known devices.

Continuing to refer to FIGS. 3 and 4, the orifices 39 of both fluid delivery elements 38A, 38B are located within a center swath or equatorial portion 41 of the treatment element 14 when the treatment element 14 is expanded, as discussed above regarding FIG. 3. Put another way, the orifices 39 are co-axially or longitudinally aligned with the equatorial portion 41. In one embodiment, the equatorial portion 41 includes the portion of the balloon(s) 20 at which the balloon(s) 20 have the largest outer diameter. Thus, during use, the coolant may be delivered to the portion of the balloon(s) 20 (and in some embodiments only to the portion of the balloon(s) 20) that are, or are most likely to be, in contact with the targeted tissue. The configurations shown in FIGS. 2-4 may cause coolant to be directed to the area(s) of the balloon(s) 20 (i.e. the equatorial portion 41) that are most likely to create circumferential lesions in bronchial tissue to achieve bronchial denervation. Further, as each orifice 39 has a relatively small diameter, the increased number of orifices 39 and the placement of the orifices 39 within the equatorial portion 41 preserve cooling efficiently and total amount of coolant flow.

Referring now to FIGS. 5A-7B, further exemplary embodiments of fluid delivery elements are shown. In the embodiments shown in FIGS. 5A-7B, the fluid delivery element 38 is a plurality of orifices 39 within the shaft 32 (that is, extending through a wall of the shaft 32 from an outer surface to a lumen within the shaft 32), rather than including a fluid delivery conduit wound about the shaft, as shown in FIGS. 3 and 4. However, it will be understood that the orifices 39 of the fluid delivery conduits 38 shown in FIGS. 2-4 may have the configuration(s) shown in FIGS. 5A-7B. For example, in one embodiment the orifices 39 are radially arranged about an entirety of the circumference of the fluid delivery element 38 (such as in a configuration shown in FIGS. 5A and 5B), in one embodiment the orifices 39 are radially arranged about a portion of the circumference of the fluid delivery element 38 (such as in a configuration shown in FIGS. 6A and 6B), and in one embodiment the orifices 39 are helically or spirally arranged about at least a portion of the circumference of the fluid delivery element 38

(such as in a configuration shown in FIGS. 7A and 7B). Likewise, the fluid delivery conduits 38 shown in FIGS. 5A-7B may include the number of orifices 39 and/or placement within the equatorial portion 41 of the balloon(s) 20 as discussed above regarding FIGS. 2-4.

In the embodiment shown in FIGS. 5A and 5B, the fluid delivery element 38 is a plurality of orifices 39 within the shaft 32, and the plurality of orifices 39 are arranged such that the orifices 39 circumscribe the shaft 32 at at least one location. In one embodiment, the plurality of orifices 39 are within a distal portion of the shaft 32 that is at least partially located within the balloon 20. This configuration produces a circular fluid delivery pattern onto the inner surface of the balloon 20 (in one embodiment, onto the inner surface of the inner balloon 20A) to create a circular lesion in the bronchial tissue, such as that shown in FIG. 14. In the embodiment shown in FIGS. 6A and 6B, the fluid delivery element 38 is a plurality of orifices 39 within the shaft 32, and the plurality of orifices 39 are arranged such that the orifices 39 partially circumscribe the shaft 32 at at least one location. In one embodiment, the orifices 39 extend around approximately half of the circumference of the shaft 32, and produce a semi-circular fluid delivery pattern onto the inner surface of the balloon 20 (in one embodiment, onto the inner surface of the inner balloon 20A) to create a semi-circular lesion in the bronchial tissue, such as that shown in FIG. 15. In the embodiment shown in FIGS. 7A and 7B, the fluid delivery element 38 is a plurality of orifices 39 within the shaft 32, and the plurality of orifices 39 are arranged such that the orifices 39 extend around the shaft 32 at least once in a helical or spiral arrangement at at least one location on the shaft 32. This configuration produces a helical or spiral fluid delivery pattern onto the inner surface of the balloon 20 (in one embodiment, onto the inner surface of the inner balloon 20A) to create helical or spiral lesion in the bronchial tissue, such as that shown in FIG. 17. Although the embodiments of FIGS. 5A-7B each include a plurality of orifices 39 within the shaft 32 (that is, extending through the shaft wall), it will be understood that the fluid delivery element 38 may have other shapes or configurations, such as a separate fluid delivery element 38 that wraps around shaft 32, as shown in FIG. 1, to produce the same fluid delivery patterns discussed herein.

In another embodiment, as shown in FIGS. 8 and 9, the treatment element 14 includes a plurality of splines 48 that are arranged about the elongate body longitudinal axis 26 and a single balloon 20 having a plurality of lobes 50 that are radially arranged about the elongate body longitudinal axis 26, between the splines 48. The splines 48 may be composed of a material that is less thermally conductive than the balloon 20. In one embodiment, the lobes 50 are elongate and extend parallel to the elongate body longitudinal axis 26. Alternatively, the treatment element 14 may include a plurality of individual balloons 20 radially arranged about the elongate body longitudinal axis 26 and between the splines 48, each of the plurality of balloons 20 forming a lobe 50. Alternatively, the treatment element 14 may include a single balloon 20 that is not manufactured or constructed with lobes but, when inflated, extends from the elongate body 24 in the areas between the splines 48 to create a plurality of lobed areas 50 of the treatment element 14. In one embodiment, the lobes 50 and the splines 48 extend parallel to the elongate body longitudinal axis 26. Unlike the balloons shown in FIG. 2, both the distal portion(s) and the proximal portion(s) of the balloon(s) 20 (and the splines 48) of the embodiment of FIGS. 8 and 9 are coupled to the distal portion 30 of the elongate body 24, and are not coupled to a shaft 32. However, it will be understood that the cryoablation device 12 shown in FIGS. 8 and 9 may include a shaft 32, at least a portion of which is coupled to the balloon(s) 20 and/or the splines 48. During use, coolant is circulated within the balloon(s) 20 to cool the balloon(s) to a temperature that is sufficient to cryoablate and, consequently, denervate adjacent targeted tissue.

Figure 10:
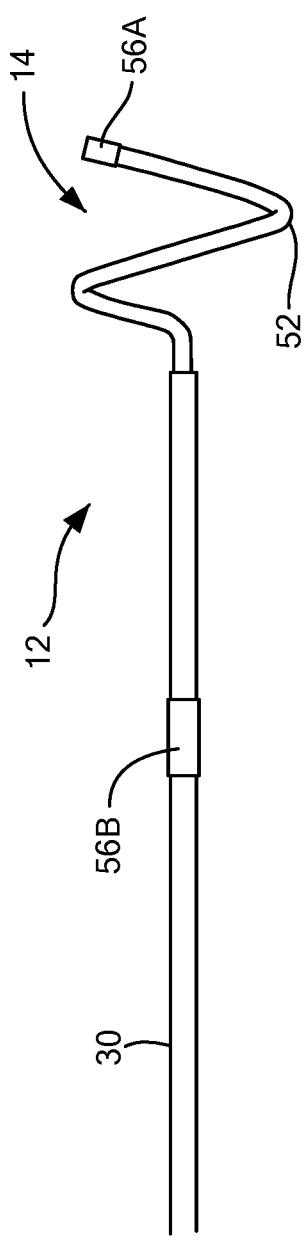
FIG. 10 shows a side view of another exemplary embodiment of a cryoablation device in accordance with the present disclosure.
Figure 11:
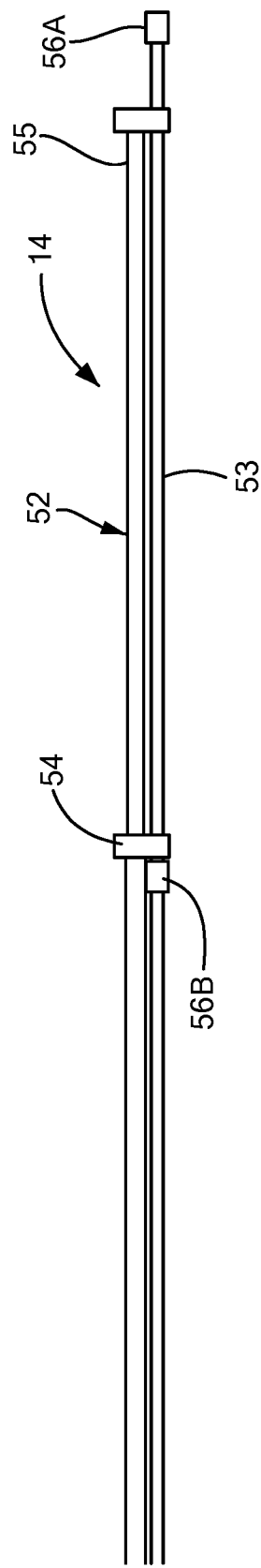
FIG. 11 shows a side view of another exemplary embodiment of a cryoablation device in a delivery configuration in accordance with the present disclosure.
Figure 12:
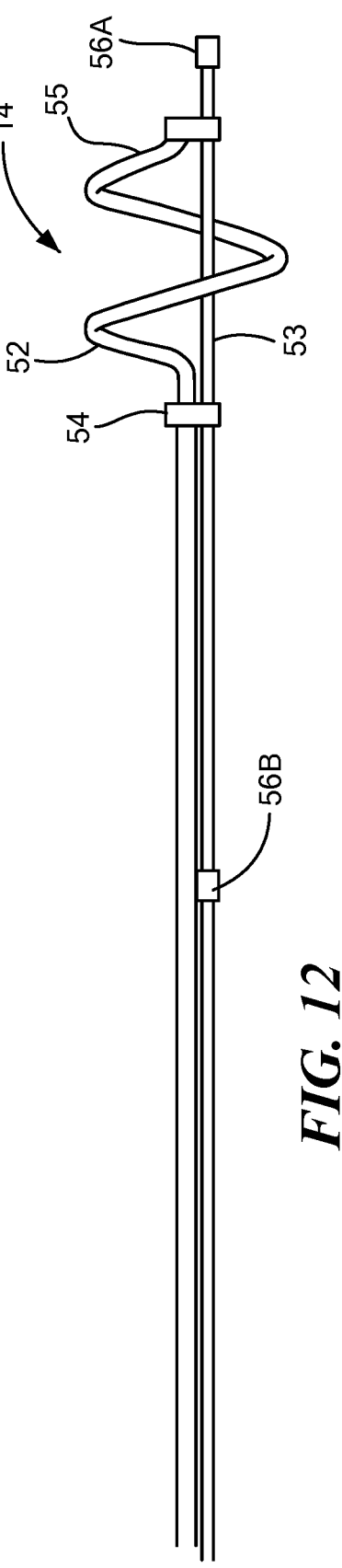
FIG. 12 shows a side view of exemplary embodiment of the cryoablation device of FIG. 11 in an expanded configuration in accordance with the present disclosure.

In another embodiment, as shown in FIGS. 10-12, the treatment element 14 includes a flexible segment 52 that is transitionable between a delivery (or first) configuration in which the flexible segment 52 is in a linear, or at least substantially linear, configuration, and an expanded (or second) configuration in which the flexible segment 52 is in a helical (for example, as shown in FIG. 10), spiral, curvilinear, or other configuration. The flexible segment 52 is composed of a thermally conductive material and includes one or more lumens or expansion chambers therein (referred to as the interior chamber 40), such that coolant is circulated within the flexible segment 52 to cool the flexible segment 52 to a temperature that is sufficient to cryoablated and, consequently, denervate adjacent targeted tissue. In the embodiment shown in FIG. 10, the flexible segment 52 is composed of a shape-memory material or a material that is biased toward the expanded configuration (or includes therein a shaping element, the shape of which controls the shape of the flexible segment 52) such that the flexible segment 52 transitions from the delivery configuration to the expanded configuration when extended out of the elongate body 24 and/or a delivery sheath.

The cryoablation device 12 shown in FIGS. 11 and 12 includes a shaft 53 slidably disposed within the elongate body 24 or coupled to the outside of, and slidably movable with respect to, the elongate body 24 (for example, as shown in FIGS. 11 and 12). In one embodiment, the shaft 53 is movably coupled to the elongate body 24 using one or more coupling elements 54, such as rings, annular guides, or the like. Further, the flexible segment 52 includes a distal portion 55 that is fixedly coupled to both the shaft 53 and the elongate body distal portion 30. Retraction of the shaft 53 within or relative to the elongate body 24 causes the flexible segment 52 to transition between the delivery configuration and the expanded configuration.

In either the embodiment of FIG. 10 or that of FIGS. 11 and 12, the flexible segment 52 has a size and shape of the bronchus to be treated. Further, the flexible segment 52, when in the expanded configuration, may have a helical shape with any number of windings. In one embodiment, the flexible segment 52 includes one winding. In another embodiment, the flexible segment 52 includes a plurality of windings. However, it will be understood that the cryoablation device 12 may include a treatment element 14 of any suitable size, number, shape, or configuration for ablating tissue from within a bronchus of a lung.

In any embodiment, the cryoablation device 12 optionally may include at least two recording electrodes 56 capable of stimulating tissue, sensing, and/or recording electrical action potential signals from within the smooth muscle tissue of the bronchi. The recording electrode(s) 56 are in communication with and transmit signals to the electromyography system 18, which interprets those signals and communicates them to the user, as is discussed in greater detail below. In one embodiment, the cryoablation device 12 includes a first recording electrode 56A located distal to the treatment element 14 and a second recording electrode 56B located proximal to the treatment element 14 (for example, as shown in FIGS. 2, 8, and 10-12). Each recording electrode 56 records the smooth muscle action potential, and the combined electromyogram signal represents a potential (voltage) difference between the action potentials recorded by the electrodes. In one embodiment, the first recording electrode 56A is coupled to the distal portion 55 of the flexible segment 52 and the second recording electrode 56B is coupled to the elongate body distal portion 30 (for example, as shown in FIG. 10). In another embodiment, the first recording electrode 56A is coupled to the distal portion of the shaft 53 and the second recording electrode 56B is coupled to the shaft 53 at a location proximal to the first recording electrode 56A (for example, as shown in FIGS. 11 and 12). However, it will be understood that the recording electrodes 56 may be at any suitable location on the cryoablation device 12.

Referring again to FIG. 1, the electromyography system 18 includes one or more controllers, processors, and/or software modules containing instructions or algorithms to provide for the automated operation and performance of the features, sequences, or procedures described herein. In one embodiment, for example, the electromyography system 18 includes processing circuitry 57 with a memory and a processor. The memory is in electrical communication with the processor and includes instructions that, when executed by the processor, configure the processor to receive, process, or otherwise use signals from the cryoablation device 12 and/or other system components. Still further, the electromyography system 18 may include one or more user input devices, controllers, speakers, and/or displays 58 for collecting and conveying information from and to the user. Additionally or alternatively, the electromyography system 18 may be in communication with the control unit 16 such that information is received and/or communicated from the electromyography system 18 to the user through the control unit 16.

In one non-limiting example, the processing circuitry 57 of the electromyography system 18 is configured to receive data (for example, electrical action potential signals) from the recording electrodes 56 of the cryoablation device 12 and to convert that data into information that can be conveyed to the user, such as a visual display, an audio signal, or the like. Further, the processing circuitry 57 of the electromyography system 18 may be configured to compare data received from the recording electrodes 56 to one or more reference values or ranges and generate an alert based on the comparison. For example, the processing circuitry of the electromyography system 18 may compare electrogram signal voltage and/or electromyogram signal amplitude over time (AOT) received from the recording electrodes to a threshold or reference electrogram signal voltage and/or electromyogram signal AOT that indicates denervation has occurred. If the received electromyogram signal voltage and/or AOT is within a threshold range of the reference electromyogram signal voltage and/or AOT, the processing circuitry may then generate and communicate an alert (such as a visual display or audio tone) to the user that indicates denervation has occurred and the user may cease the cryoablation procedure. Additionally, the processing circuitry 57 of the electromyography system 18 may be configured to calculate a time to denervation based on the difference between the received and the reference electromyography signal voltage and/or AOTs, so the user can know how much longer the cryoablation procedure should continue.

As used herein, the term "control unit" for simplicity may include any system components that are not part of the cryoablation device 12 itself, other than components of the electromyography system 18, regardless of whether the component is physically located within or external to the control unit 16. Further, the electromyography system 18 may be a standalone system in communication with the control unit 16 or may be contained within or integrated with the control unit 16, even though it is shown as being physically separated from the control unit 16 in FIG. 1. In one embodiment, the control unit 16 includes a coolant supply reservoir 44, a coolant recovery reservoir 46 or an exhaust or scavenging system for recovering or venting expended fluid for re-use or disposal, as well as various control mechanisms. In addition to providing an exhaust function for the coolant supply, the control unit 16 may also include pumps, valves, controllers or the like to recover and/or re-circulate fluid delivered to the elongate body 24 and/or the fluid pathways of the system. Further, the control unit 16 may include a vacuum pump 60 for creating a low-pressure environment in one or more conduits within the cryoablation device 12 so that coolant is drawn into the conduit(s)/lumen(s) of the elongate body 24, away from the distal portion 30 and towards the proximal portion 28 of the elongate body 24.

In one embodiment, the control unit 16 includes one or more controllers, processors, and/or software modules containing instructions or algorithms to provide for the automated operation and performance of the features, sequences, or procedures described herein. In one embodiment, for example, the control unit 16 includes processing circuitry 62 programmed or programmable to execute the automated or semi-automated operation and performance of the features, sequences, calculations, or procedures described herein. In one embodiment, for example, the control unit 16 includes processing circuitry 62 with a memory and a processor. The memory is in electrical communication with the processor and includes instructions that, when executed by the processor, configure the processor to receive, process, or otherwise use signals from the cryoablation device 12 and/or other system components. Still further, the control unit 16 may include one or more user input devices, controllers, speakers, and/or displays 64 for collecting and conveying information from and to the user.

Although not shown, the medical system 10 may include one or more sensors to monitor the operating parameters through the medical system 10, such as pressure, temperature, coolant flow rate, or the like. The sensor(s) may be in communication with the control unit 16 for initiating or triggering one or more alerts or coolant delivery modifications during operation of the cryoablation device 12.

Figure 13:
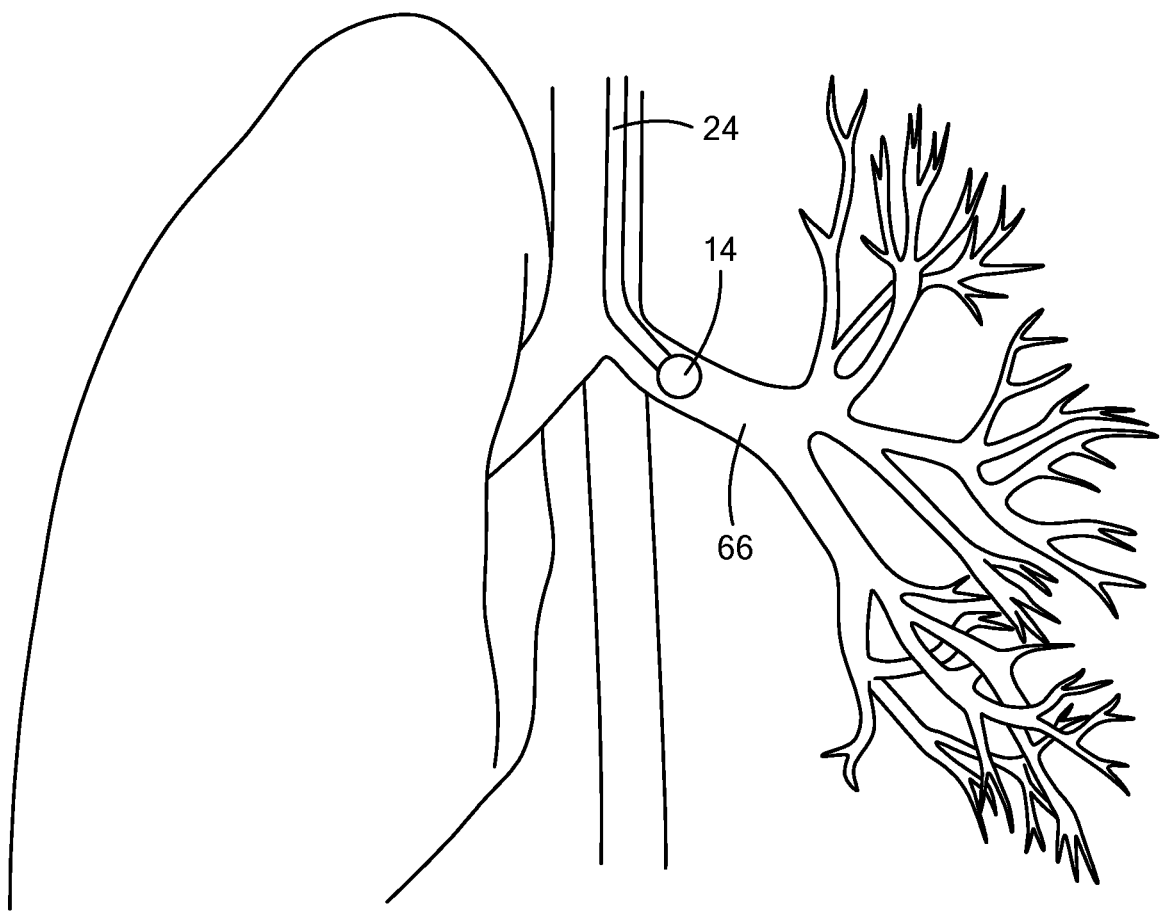
FIG. 13 shows a cryoablation device positioned at an exemplary treatment site within a bronchus in accordance with the present disclosure.
Figure 18:
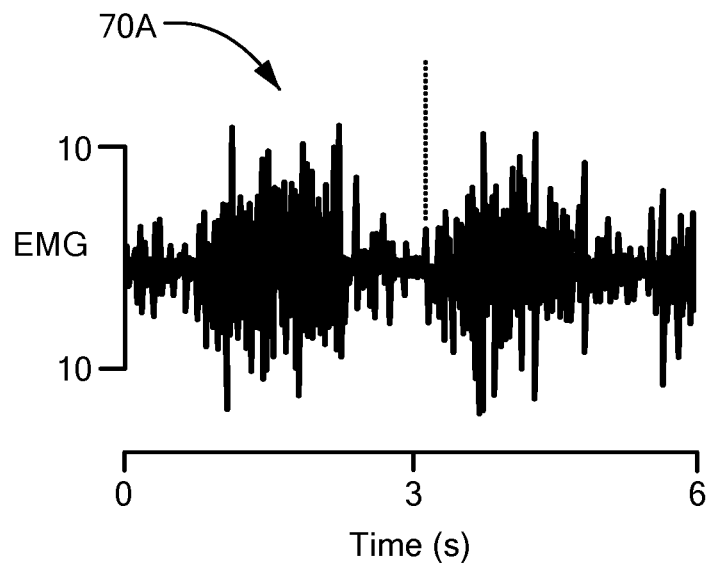
FIG. 18 shows an exemplary electromyogram before bronchial denervation.
Figure 19:
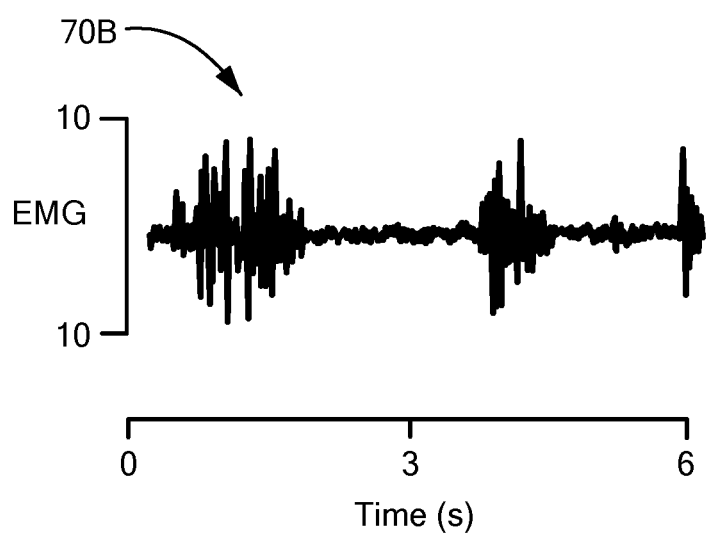
FIG. 19 shows another exemplary electromyogram after bronchial denervation in accordance with the present disclosure.
Figure 20:
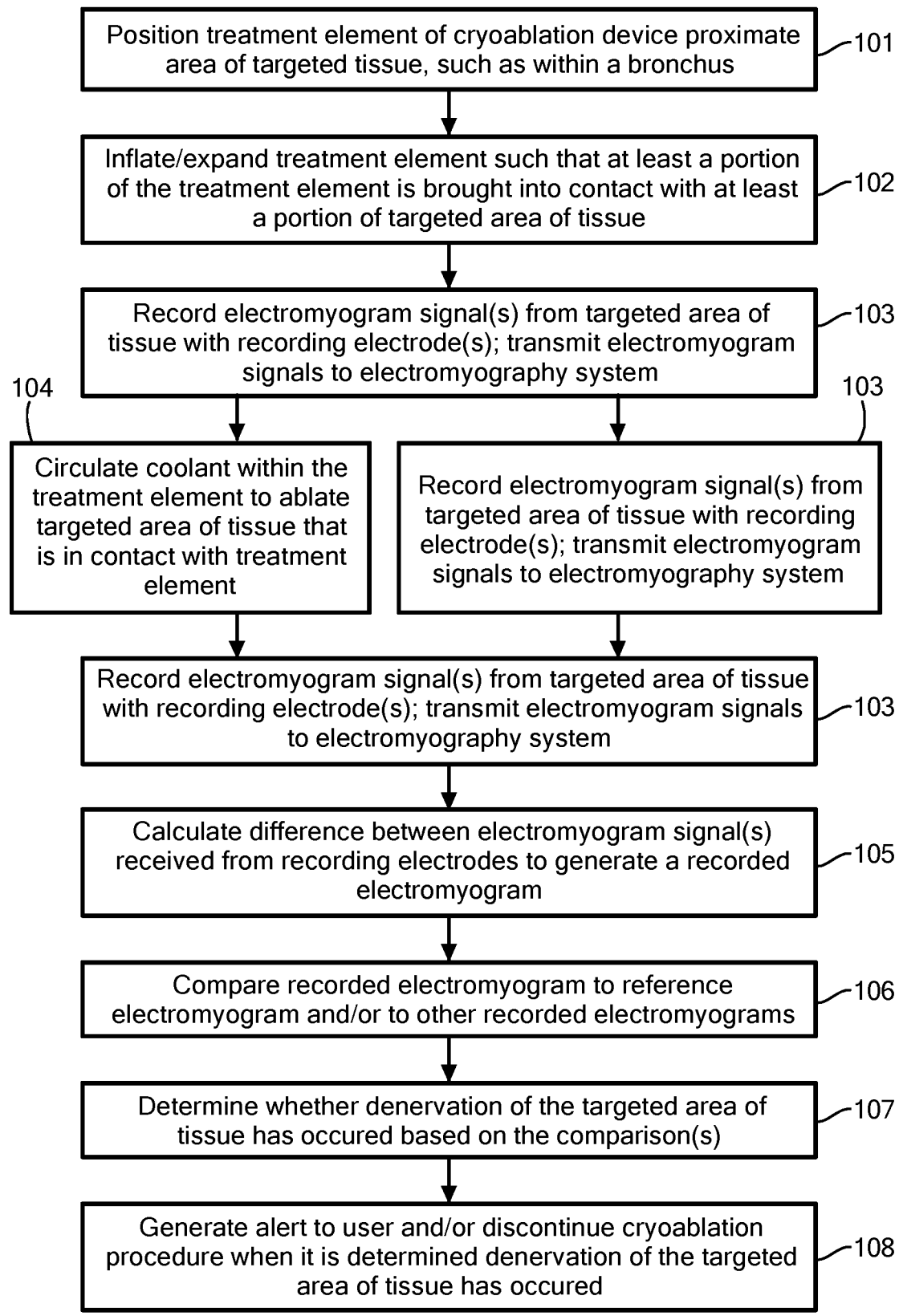
FIG. 20 shows an exemplary method of performing bronchial denervation using a cryoablation device in accordance with the present disclosure.

Referring now to FIG. 20, with reference to FIGS. 13-19, an exemplary method of performing bronchial denervation using a cryoablation device 12 is shown. In a first step 101, a treatment element 14 of a cryoablation device 12 is positioned within a bronchus 66 of the patient's lung at a location proximate a targeted area of tissue (for example, as shown in FIG. 13). In a second step 102, the treatment element 14 of the cryoablation device 12 is inflated, expanded, or otherwise manipulated such that at least a portion of the treatment element 14 is brought into contact with at least a portion of the targeted area of tissue.

In a third step 103, the recording electrodes 56 are positioned such that they are in contact with the targeted area of tissue and are used to record electromyogram signals (smooth muscle action potential signals) from the targeted area of tissue. Further, the electrogram signals may be recorded by the recording electrodes before, during, and/or after a cryoablation procedure. Thus, the third step 103 may occur at any time during the method.

Figure 14:
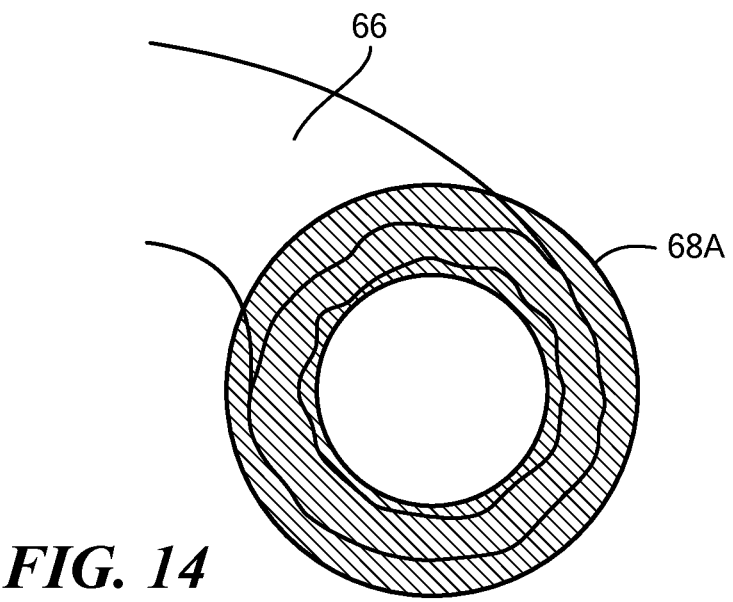
FIG. 14 shows an exemplary lesion pattern created within a bronchus by a cryoablation device in accordance with the present disclosure.
Figure 15:
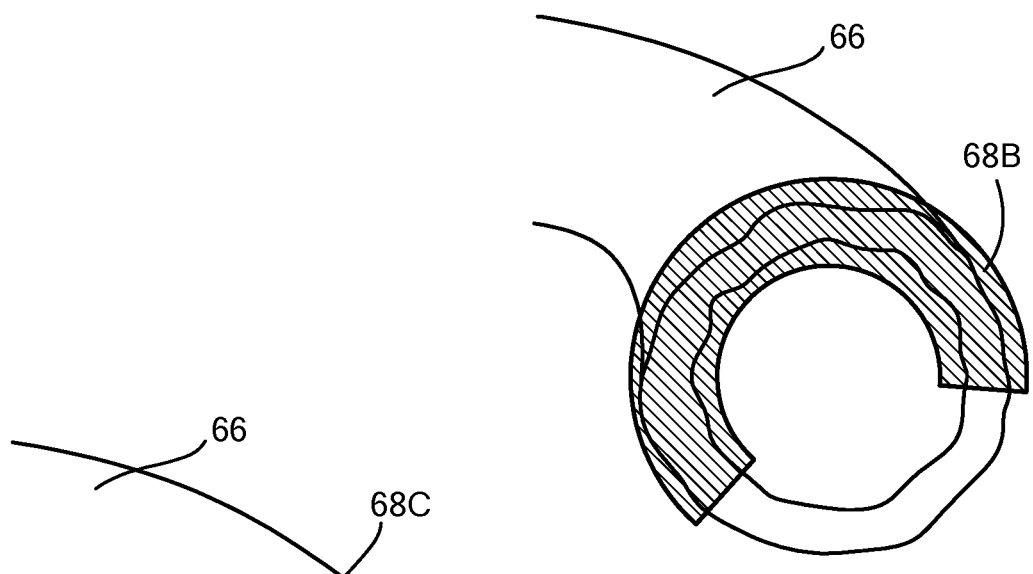
FIG. 15 shows another exemplary lesion pattern created within a bronchus by a cryoablation device in accordance with the present disclosure.
Figure 16:
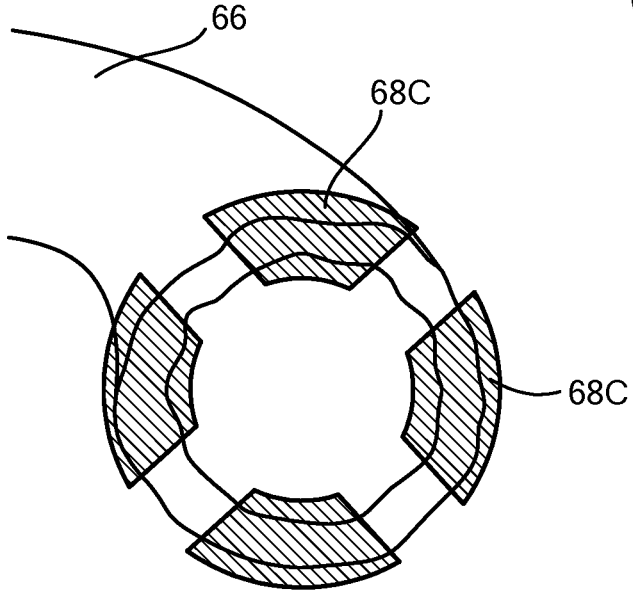
FIG. 16 shows another exemplary lesion pattern created within a bronchus by a cryoablation device in accordance with the present disclosure.
Figure 17:
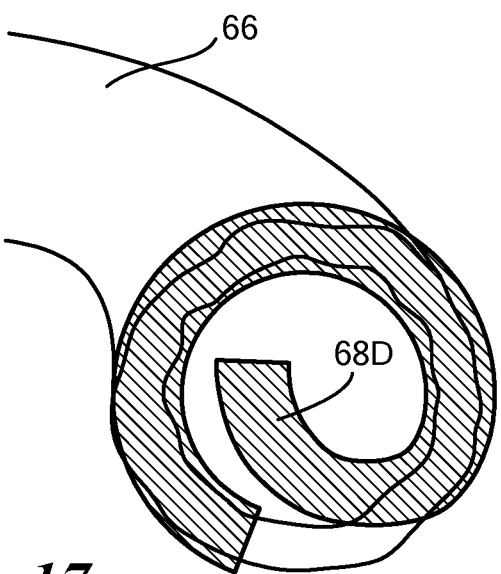
FIG. 17 shows another exemplary lesion pattern created within a bronchus by a cryoablation device in accordance with the present disclosure.

In a fourth step 104, coolant is delivered from the coolant supply reservoir 44 to the treatment element 14 and circulated within the treatment element 14 to reduce the temperature of the treatment element 14 to a temperature sufficient to cryoablate tissue that is in contact with the treatment element 14. As noted above, the recording electrodes 56 may continue to record electromyogram signals from the bronchial tissue over the time during which coolant is circulated within the treatment element 14 (that is, during the cryoablation procedure). This is indicated as step 103 in FIG. 20; however, it will be understood that this step may be performed at the same time as, before, and/or after the fourth step 104. Non-limiting examples of ablation patterns created within bronchial tissue by a treatment element 14 are shown in FIGS. 14-17. For example, using a treatment element 14 such as that shown and described in FIGS. 1 and 2 (that is, at least one balloon 20 without lobes) that has, in one embodiment, a fluid delivery element 38 with a circular fluid delivery pattern (as shown in FIGS. 5A and 5B), may create a circumferential lesion 68A within the bronchial tissue 66, a stylized representation of which is shown in FIG. 14; using a treatment element 14 such as that shown and described in FIGS. 1 and 2 that has, in one embodiment, a fluid delivery element 38 with a semi-circular fluid delivery pattern (as shown in FIGS. 6A and 6B), may create a partially circumferential or semi-circular lesion 68B (for example, a semi-circular lesion) within the bronchial tissue 66, a stylized representation of which is shown in FIG. 15; using a treatment element 14 such as that shown and described in FIGS. 8 and 9 (that is, a balloon with lobes 50 or several balloons forming lobed areas 50) may create a series of lesions 68C within the bronchial tissue 66, a stylized representation of which is shown in FIG. 16, or an interrupted circumferential lesion such as that shown in FIG. 14; and using a treatment element 14 such as shat shown and described in FIG. 10 (that is, a flexible segment 52 transitionable to a helical configuration) or a treatment element 14 such as that shown and described in FIGS. 1 and 2 that has, in one embodiment, a fluid delivery element 38 with a spiral or helical fluid delivery pattern (as shown in FIGS. 7A and 7B) may create a helical lesion 68D in the bronchial tissue 66, a stylized representation of which is shown in FIG. 17.

Here, the third step 103 may again be performed. The electromyogram signals are transmitted from the recording electrodes 56 to the electromyography system 18. Additionally, these signals may be continually recorded and transmitted before, during, and after the cryoablation procedure. The processing circuitry 57 of the electromyography system 18 then uses the received electromyogram signals to make one or more comparisons and determinations (thus, the received electromyogram signals may be referred to as being raw electromyogram signals). For example, in a fifth step 105, the processing circuitry 57 of the electromyography system 18 calculates a difference between at least one electromyogram signal received from a first recording electrode 56A and at least one electromyogram signal received from a second recording electrode 56B. In one non-limiting example, the processing circuitry 57 of the electromyography system 18 calculates a voltage difference between received or raw electrogram signals transmitted from the recording electrodes during the cryoablation procedure and generates a recorded electromyogram 70. Thus, the recorded electromyogram 70 includes voltage difference(s) over time. For example, FIG. 18 shows a recorded electromyogram 70A recorded before denervation occurs (that is, recorded before the cryoablation procedure and/or during the cryoablation procedure, before denervation occurs). As noted above, the recording electrodes 56 may continue to record electrogram signals during and/or after the cryoablation procedure, and the processing circuitry 57 of the electromyography system 18 may continue to generate recorded electromyograms 70.

Further, in one embodiment, the processing circuitry 57 of the electromyography system 18 is configured to compare a recorded electromyogram 70 generated from electromyogram signals received before the cryoablation procedure with a recorded electromyogram 70 generated from electromyogram signals received during and/or after the cryoablation procedure, and to use this comparison to determine whether denervation of the bronchial tissue 66 has occurred (such as in a sixth step 106). In one non-limiting example, if the difference in recorded electromyograms (such as a voltage difference) exceeds a threshold difference, the processing circuitry 57 of the electromyography system 18 may determine that denervation has occurred (such as in a seventh step 107). Additionally or alternatively, the processing circuitry 57 electromyography system 18 is configured to compare a recorded electromyogram 70 generated from electromyogram signals received during and/or after a cryoablation procedure with a reference electromyogram that indicates denervation has occurred. If the recorded electromyogram 70 is the same as, or is within a threshold range or difference of, the reference electromyogram, the processing circuitry 57 of the electromyography system 18 may determine that denervation has occurred (such as in a seventh step 107). For example, FIG. 19 shows a recorded electromyogram 70B after denervation has occurred, in which the attenuated electromyogram voltage is shown.

In an eighth step 108, the processing circuitry 57 of the electromyography system 18 generates an alert when it determines that denervation has occurred. In one non-limiting example, the electromyography system 18 generates an audible and/or visual alert that communicates to the user that denervation has occurred and gives the user the opportunity to discontinue the cryoablation procedure (for example, to discontinue or reduce the circulation of coolant within the treatment element 14). Additionally or alternatively, the electromyography system 18 generates an alert in the form of alert data and transmits this data to the control unit 16. The control unit 16 may then communicate the alert (for example, audible and/or visual alert) to the user to prompt the user to manually discontinue the cryoablation procedure, and/or the control unit 16 may automatically discontinue or reduce the circulation of coolant within the treatment element 14 to end the cryoablation procedure.

It will be appreciated by persons skilled in the art that the present embodiments are not limited to what has been particularly shown and described herein above. In addition, unless mention was made above to the contrary, it should be noted that all of the accompanying drawings are not to scale. A variety of modifications and variations are possible in light of the above teachings.

It should be understood that various aspects disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single module or unit for purposes of clarity, it should be understood that the techniques of this disclosure may be performed by a combination of units or modules associated with, for example, a medical device.

In one or more examples, the described techniques may be implemented in hardware, software, firmware, or any combination thereof. If implemented in software, the functions may be stored as one or more instructions or code on a computer-readable medium and executed by a hardware-based processing unit. Computer-readable media may include non-transitory computer-readable media, which corresponds to a tangible medium such as data storage media (e.g., RAM, ROM, EEPROM, flash memory, or any other medium that can be used to store desired program code in the form of instructions or data structures and that can be accessed by a computer).

Instructions may be executed by one or more processors, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" as used herein may refer to any of the foregoing structure or any other physical structure suitable for implementation of the described techniques. Also, the techniques could be fully implemented in one or more circuits or logic elements.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A system for performing bronchial denervation, the system comprising:
    an electromyography system having a cryoablation device with at least two recording electrodes,
    wherein the electromyography system is configured to:
        calculate a difference between a first electromyogram signal received from a first recording electrode and a second electromyogram signal received from a second recording electrode to generate a recorded electromyogram; and
        compare the recorded electromyogram to a reference electromyogram.

2. The system of claim 1, wherein the electromyography system is further configured to receive the first electromyogram signal and the second electromyogram signal from the cryoablation device.

3. The system of claim 2, wherein when the cryoablation device is performing a cryoablation procedure the first recording electrode and the second recording electrode are configured to continuously transmit[ting] signals to the electromyography system.

4. The system of claim 1, wherein the electromyography system is further configured to calculate a voltage difference between the first electromyogram signal and the second electromyogram signal.

5. The system of claim 1, wherein before the cryoablation device is performing a cryoablation procedure, the first recording electrode and the second recording electrode are configured to continuously transmit[ting] signals to the electromyography system.

6. The system of claim 5, while the cryoablation device performs a cryoablation procedure and after the cryoablation device performs a cryoablation procedure, the first recording electrode and the second recording electrode are configured to continuously transmit[ting] signals to the electromyography system.

7. The system of claim 1, wherein the electromyography system is configured to calculate the difference between the first electromyogram signal and the second electromyogram signal by:
    calculating a difference between the first electromyogram signal received from the first recording electrode and the second electromyogram signal received from the second recording electrode before a cryoablation procedure to generate a first recorded electromyogram; and
    calculating the difference between the first electromyogram signal received from the first recording electrode and the second electromyogram signal received from the second recording electrode after cryoablation to generate a second recorded electromyogram.

8. The system of claim 7, wherein the electromyography system is further configured to calculate the difference between the first recorded electromyogram and the second recorded electromyogram.

9. The system of claim 8, wherein the electromyography system is further configured to compare the calculated difference between the first recorded electromyogram and the second recorded electromyogram with a reference electromyogram.

10. The system of claim 9, wherein the electromyography system is further configured to compare whether denervation has occurred based on the comparison between the difference between the first recorded electromyogram and the second recorded electromyogram with the reference electromyogram.

11. The system of claim 10, wherein the electromyography system is further configured to determine that denervation has occurred when the comparison between the difference between the first recorded electromyogram and the second recorded electromyogram with the reference electromyogram exceeds a threshold difference.

12. The system of claim 11, wherein the electromyography system is further configured to generate an alert when the electromyography system determines that denervation has occurred.

13. The system of claim 12, wherein the alert is an audible or visual alert.

14. A system for performing bronchial denervation, the system comprising:
    a cryoablation device including a treatment element and a first recording electrode and a second recording electrode;
    an electromyography system in communication with the first recording electrode and the second recording electrode, the electromyography system including processing circuitry configured to:
        receive electromyogram signals from the first recording electrode and the second recording electrode;
        calculate a difference between a first electromyogram signal received from the first recording electrode and a second electromyogram signal received from the second recording electrode to generate a recorded electromyogram; and
        compare the recorded electromyogram to a reference electromyogram.

15. The system of claim 14, wherein the processing circuitry is further configured to determine whether denervation has occurred in an area of tissue based on the comparison between the recorded electromyogram and the reference electromyogram.

16. The system of claim 14, wherein the processing circuitry is further configured to generate an alert when the processing circuitry has determined that denervation has occurred in an area of tissue.

17. A method for performing bronchial denervation, the method comprising:
  positioning a treatment element proximate an area of targeted tissue;
  expanding the treatment element such that at least a portion of the treatment element is in contact the area of targeted tissue;
  circulating a coolant within the treatment element to reduce a temperature of the treatment element to a temperature sufficient to cryoablate at least a portion of the area of targeted tissue;
  recording at least one electromyogram signal from the at least a portion of the area of targeted tissue with each of a first recording electrode and a second recording electrode;
  transmitting the recorded at least one electromyogram signal to an electromyography system;
  calculating a difference between the at least one electromyogram signal received from the first recording electrode and the at least one electromyogram signal received from the second recording electrode to generate a recorded electromyogram; and
  comparing the recorded electromyogram to a reference electromyogram.

18. The method of claim 17, further comprising:
  determining whether denervation has occurred in the at least a portion of the area of targeted tissue based on the comparison; and
  discontinuing the circulation of the coolant within the treatment element when it is determined that denervation has occurred in the area of targeted tissue.

19. The method of claim 18, further comprising:
  generating an alert when it is determined that denervation has occurred in the at least a portion of the area of targeted tissue.

20. The method of claim 17, wherein the electromyography system further includes processing circuitry configured to determine whether denervation has occurred in the area of targeted tissue based on the comparison between the recorded electromyogram and the reference electromyogram.

* * * * *